United States Patent [19]

Shimizu et al.

[11] Patent Number: 5,219,736

[45] Date of Patent: Jun. 15, 1993

[54] PROCESS FOR PRODUCING 3-DEACYLATED DERIVATIVE OF 16-MEMBERED MACROLIDE ANTIBIOTIC

[75] Inventors: Akira Shimizu; Shuichi Gomi; Keiichi Ajito; Takashi Yaguchi; Eriko Tanaka; Osamu Hara; Shinji Miyadoh, all of Kanagawa, Japan

[73] Assignee: Meiji Seika Kaisha Ltd., Tokyo, Japan

[21] Appl. No.: 925,038

[22] Filed: Aug. 5, 1992

[30] Foreign Application Priority Data

Aug. 7, 1991 [JP] Japan .................... 3-197694

[51] Int. Cl.$^5$ ............ C12P 19/62; C12P 19/60; C12R 1/645
[52] U.S. Cl. .......................... 435/76; 435/74; 435/75; 536/7.1
[58] Field of Search .............. 435/74, 75, 76, 911

[56] References Cited

U.S. PATENT DOCUMENTS

| | | | |
|---|---|---|---|
| 4,092,473 | 5/1978 | Okamoto et al. | 435/76 |
| 4,201,841 | 5/1980 | Okamoto et al. | 435/76 |
| 4,205,163 | 5/1980 | Mori et al. | 536/7.1 |
| 4,559,305 | 12/1985 | Zajic et al. | |

FOREIGN PATENT DOCUMENTS 0349676 1/1990 European Pat. Off. .

OTHER PUBLICATIONS

J56 154998 (JPOABS) Nov. 30, 1951 Sakakibara et al.
Patent Abstracts of Japan, Unexamined Applications, C Field, vol. 3, No. 104, Sep. 4, 1979, p. 26 C 57, Kokai-No. 54-81 288.

*Primary Examiner*—Herbert J. Lilling
*Attorney, Agent, or Firm*—Sughrue, Mion, Zinn, Macpeak & Seas

[57] ABSTRACT

A method of producing a 3-deacylated derivative of a 16-membered macrolide antibiotic using a microorganism belonging to the genus Phialophora or Preussia which comprises incubating said microorganism with a 16-membered macrolide antibiotic in a medium containing nutritional sources commonly used for incubating microorganisms, isolating a 3-deacylated derivative from the incubation medium, a microorganism to be used for the above method and a novel macrolide antibiotic.

2 Claims, 12 Drawing Sheets

PROCESS FOR PRODUCING 3-DEACYLATED DERIVATIVE OF 16-MEMBERED MACROLIDE ANTIBIOTIC

FIELD OF THE INVENTION

This invention relates to a method of producing a 3-deacylated derivative of a 16-membered macrolide antibiotic, a microorganism to be used therefor and a novel macrolide antibiotic.

BACKGROUND OF THE INVENTION

A number of reports on microbial conversion of macrolide antibiotics have been presented hitherto. Eiki et al. reported 9-deacylation of 9-acetyljosamycin using *Streptomyces olivochromogenes* (*J. Ferment. Bioeng.*, 71, 370-372 (1991)). Omura et al. summarized 4″-deacylation of 16-membered macrolide antibiotics (J. Antibiotics, 28, 401-433 (1975)). Although 16-membered macrolide antibiotics include a number of antibiotics having an acyl group at the 3-position such as leucomycins, spiramycins, deltamycins and carbomycins, microbial 3-deacylation of these antibiotics has never been reported so far. In addition, none of the compounds provided by the present invention represented by formulae (III), (IV) and (V) shown below has been reported as a natural or synthetic compound.

It is very difficult to eliminate a 3-acyl group of a 16-membered macrolide antibiotic through a chemical reaction or with the use of an intracellular enzyme. In addition, it is known that the MIC (minimum inhibitory concentration) of a 3-deacylated substance on a gram-positive bacterium is usually lower than that of the starting compound. Therefore, it is highly important to provide a 3-deacylated derivative of a 16-membered macrolide antibiotic in order to develop a novel and useful macrolide antibiotic or to give a material to be converted into the same.

SUMMARY OF THE INVENTION

The present inventors have screened for microorganisms capable of converting a 16-membered macrolide antibiotic and have found a 3-deacylation reaction occurred with a strain belonging to the genus Phialophora or Preussia.

It is an object of the present invention to provide a method of producing a compound represented by formula (II),

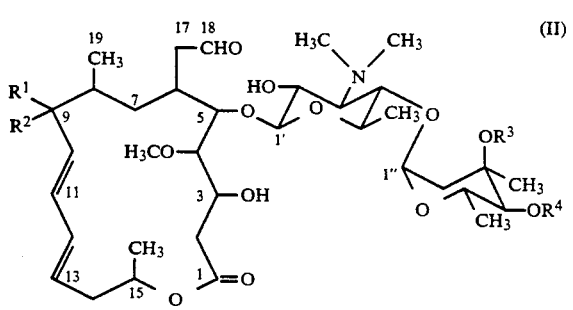

wherein $R^1$ represents a hydrogen atom, $R^2$ represents a hydroxyl group, or $R^1$ and $R^2$ form a carbonyl group together with the carbon atom of the 16-membered structure to which they are bound, $R^3$ represents a hydrogen atom or an acetyl group and $R^4$ represents a hydrogen atom, an acetyl group, a propionyl group a butyryl group or an isovaleryl group, or formula (III),

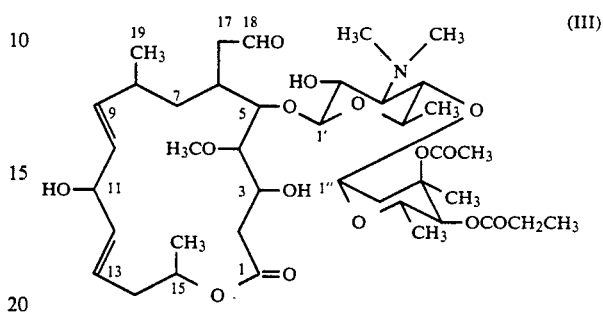

which comprises treating a compound represented by formula (I)

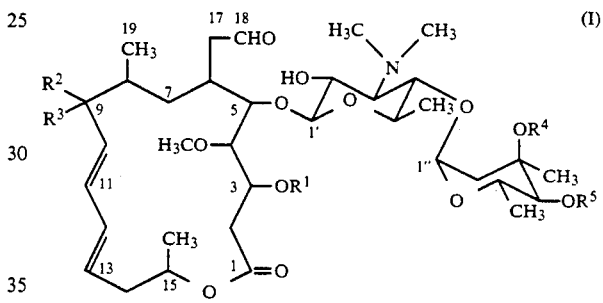

wherein $R^1$ represents an acetyl group or a propionyl group, $R^2$ represents a hydrogen atom, $R^3$ represents a hydroxyl group or an acetoxy group, or $R^2$ and $R^3$ form a carbonyl group together with the carbon atom of the 16-membered structure to which they are bound, $R^4$ represents a hydrogen atom or an acetyl group and $R^5$ represents a hydrogen atom, an acetyl group, a propionyl group, a butyryl group or an isovaleryl group, with a microorganism belonging to the genus Phialophora or Preussia.

Another object of the present invention is to provide an isolated microorganism to be used therefor.

Another object of the present invention is to provide novel macrolide antibiotics 3″-O-acetyl-3-depropionylneoisomidecamycin of formula (III), -continued

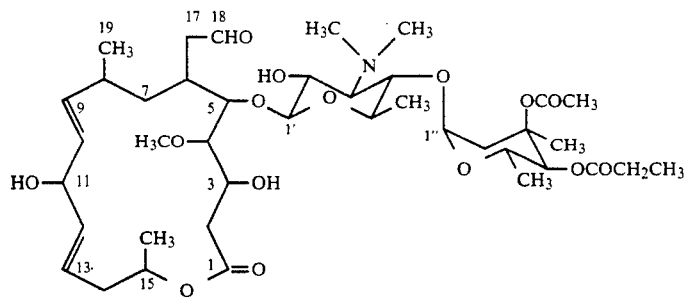

3''-O-acetylleucomycin A7 of formula (IV)

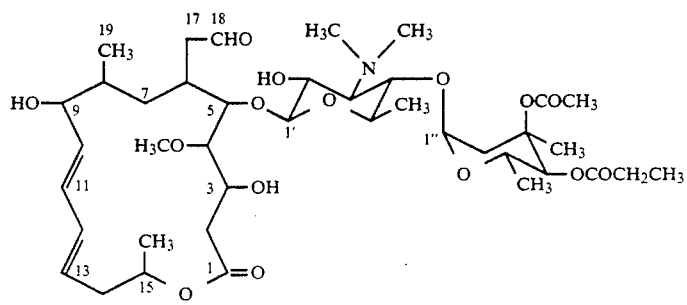

and 9-dehydroleucomycin A7 of formula (V).

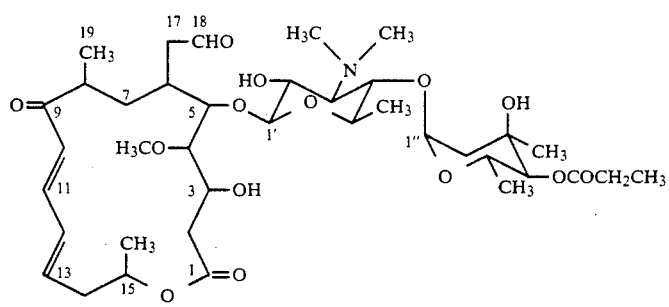

DETAILED DESCRIPTION OF THE INVENTION

Figure 1:
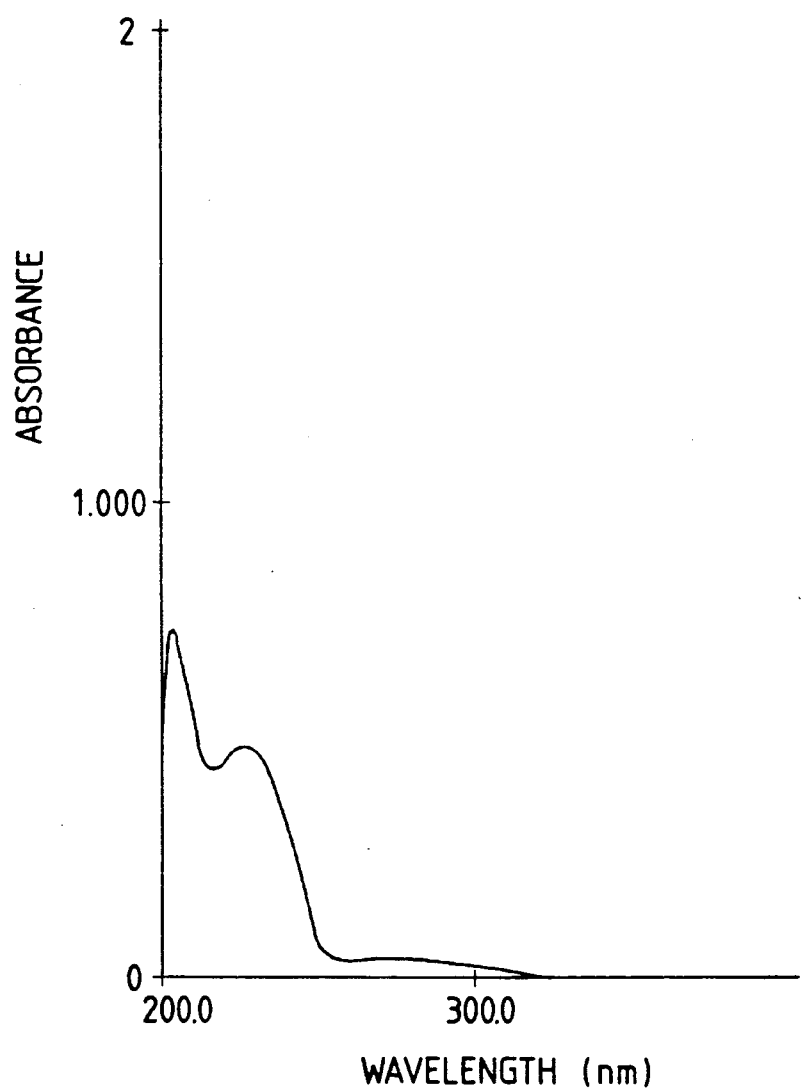
FIG. 1 is the UV absorption spectrum of the compound of formula (III) in methanol (100 μg/ml).
Figure 2:
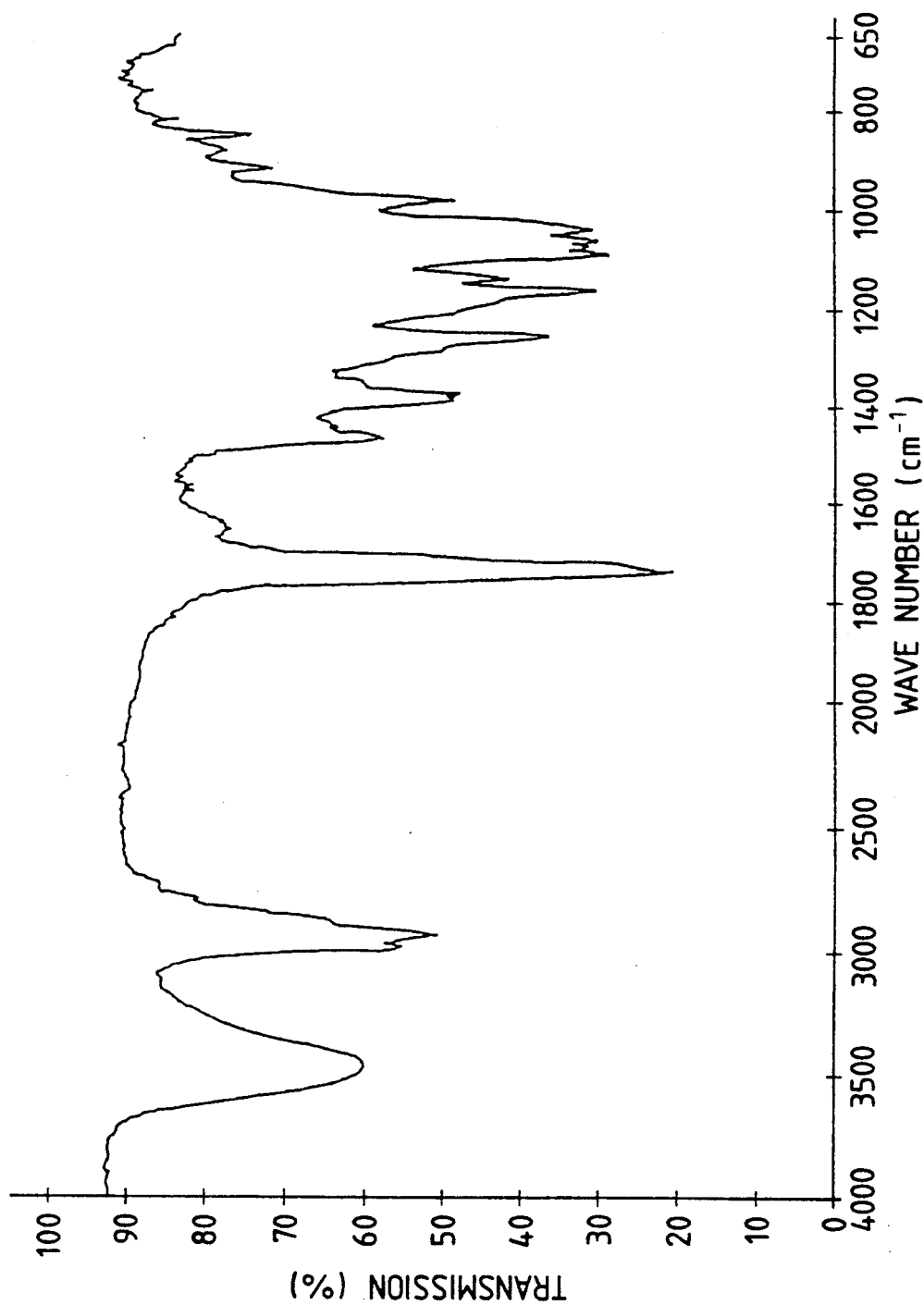
FIG. 2 is the IR absorption spectrum of the compound of formula (III) in potassium bromide tablets.
Figure 3:
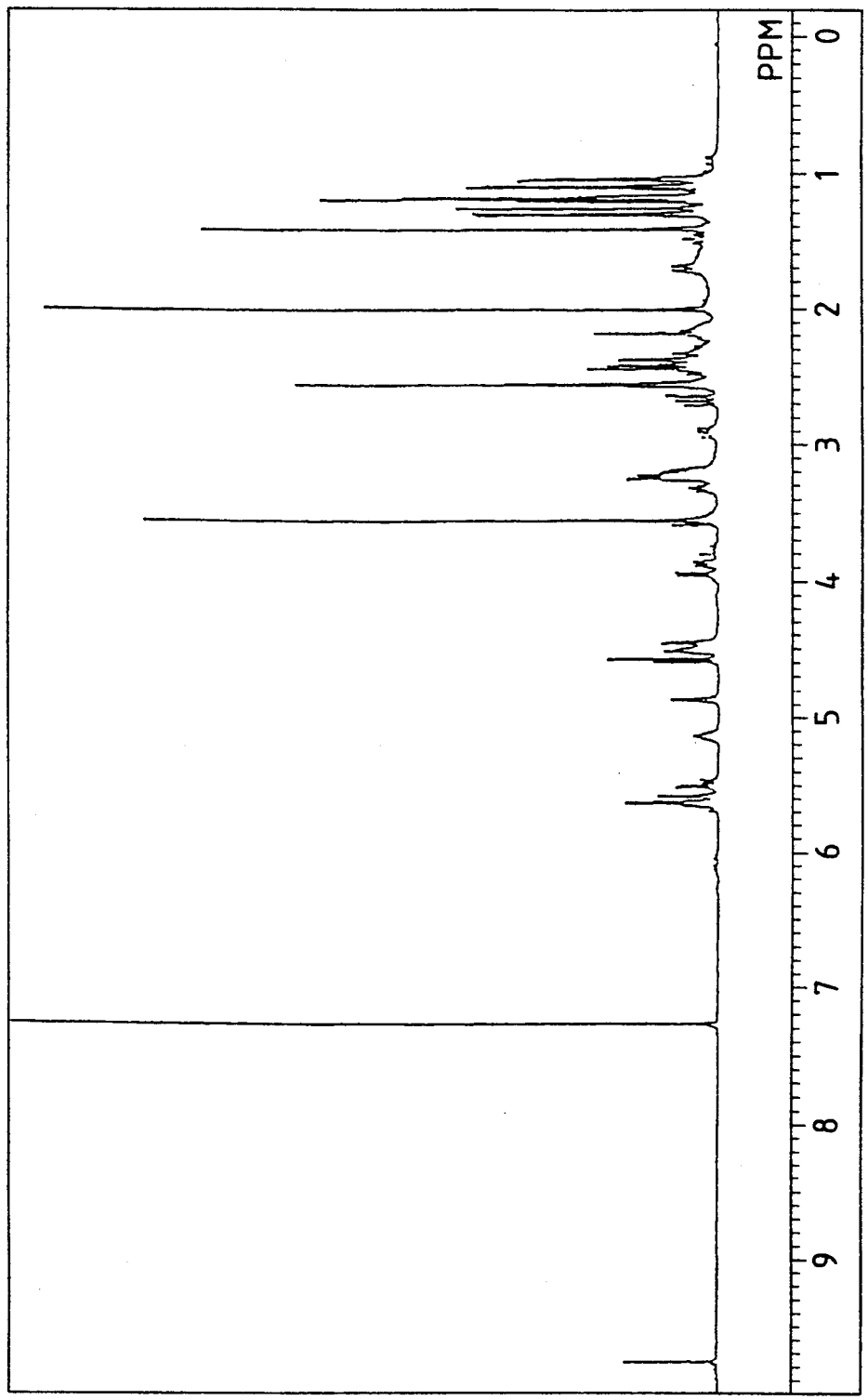
FIG. 3 is the 400 MHz $^1$H-NMR spectrum of the compound of formula (III) in a deuterated chloroform solution.
Figure 4:
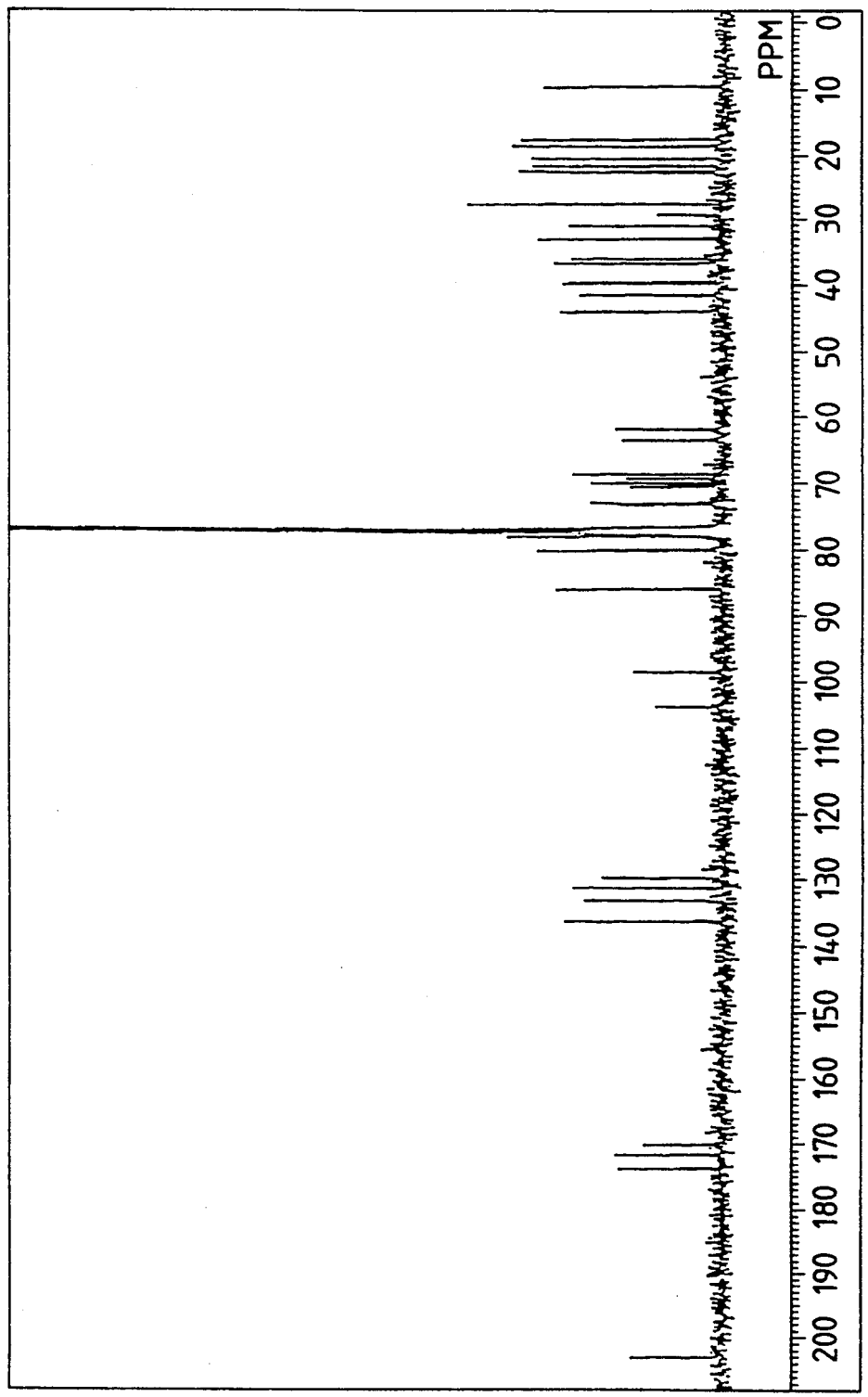
FIG. 4 is the 100 MHz $^{13}$C-NMR spectrum of the compound of formula (III) in a deuterated chloroform solution.
Figure 5:
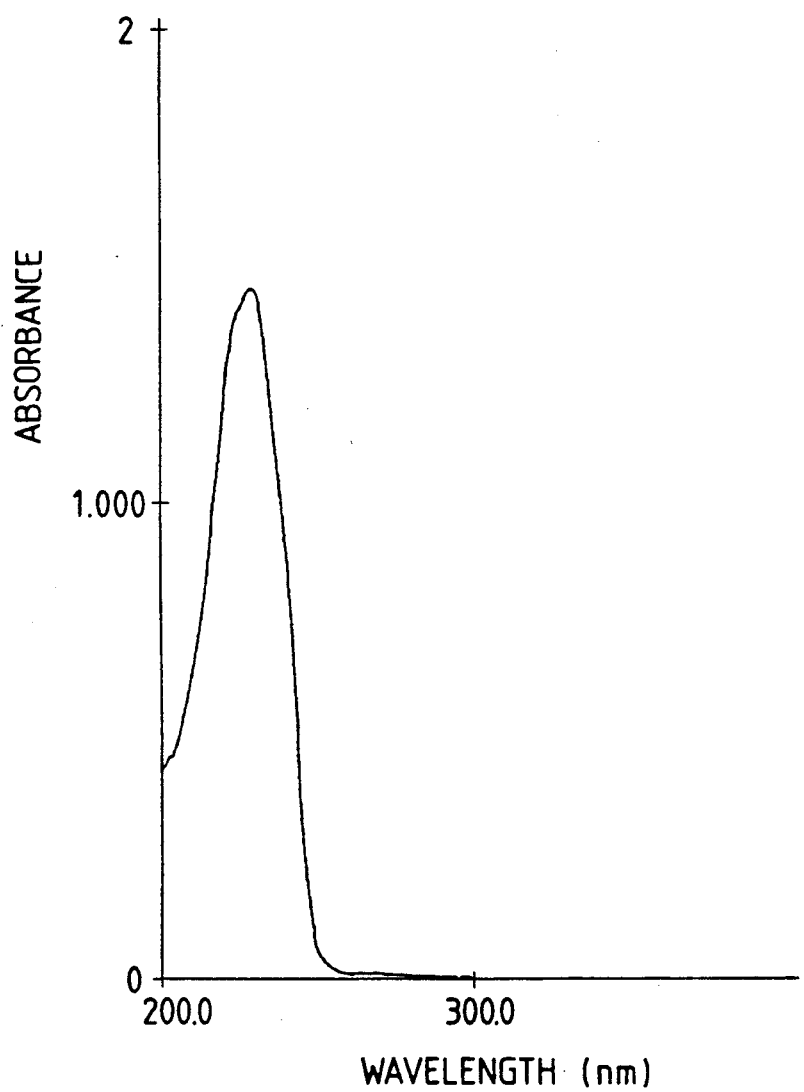
FIG. 5 is the UV absorption spectrum of the compound of formula (IV) in methanol (50 μg/ml).
Figure 6:
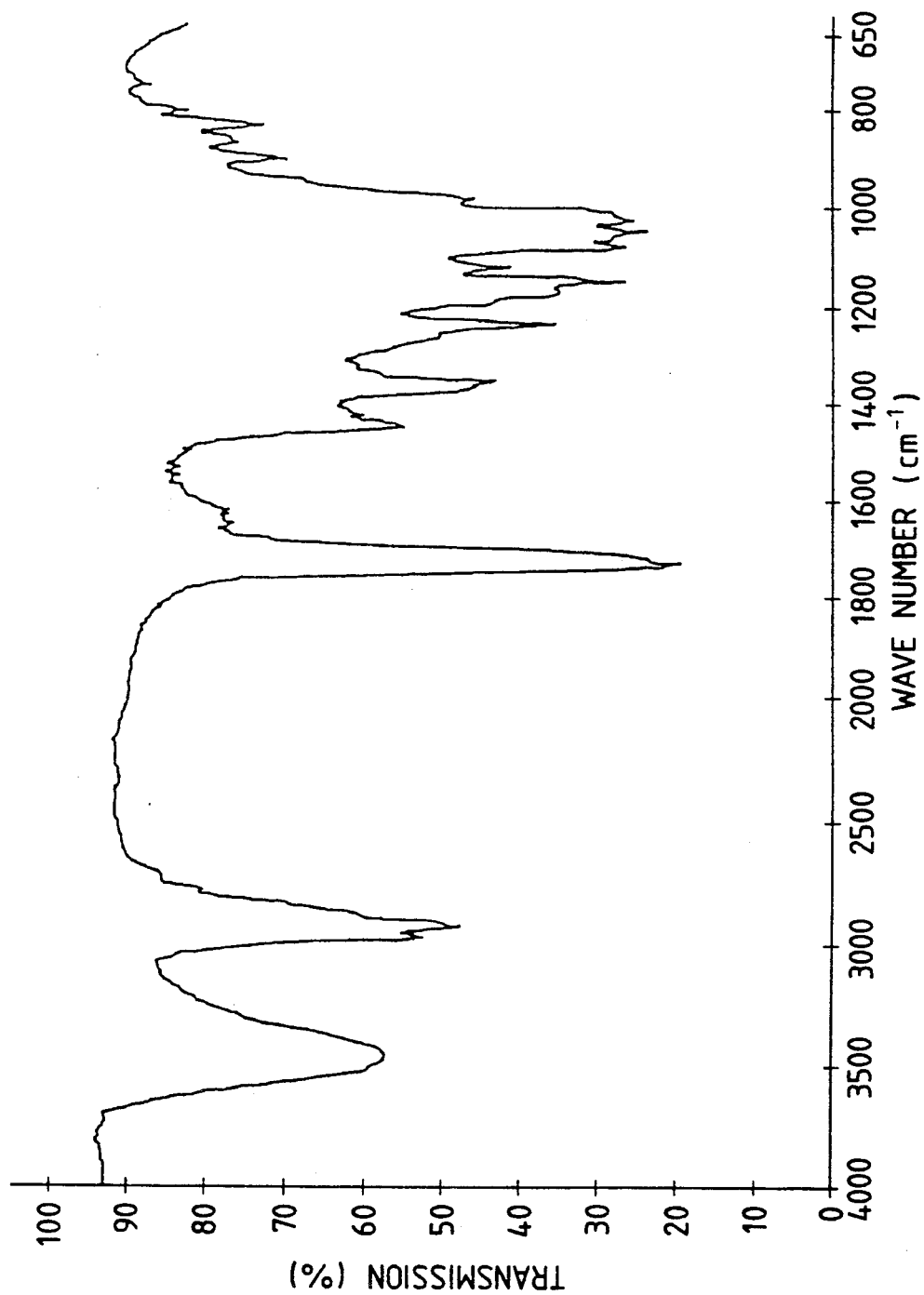
FIG. 6 is the IR absorption spectrum of the compound of formula (IV) in potassium bromide tablets.
Figure 7:
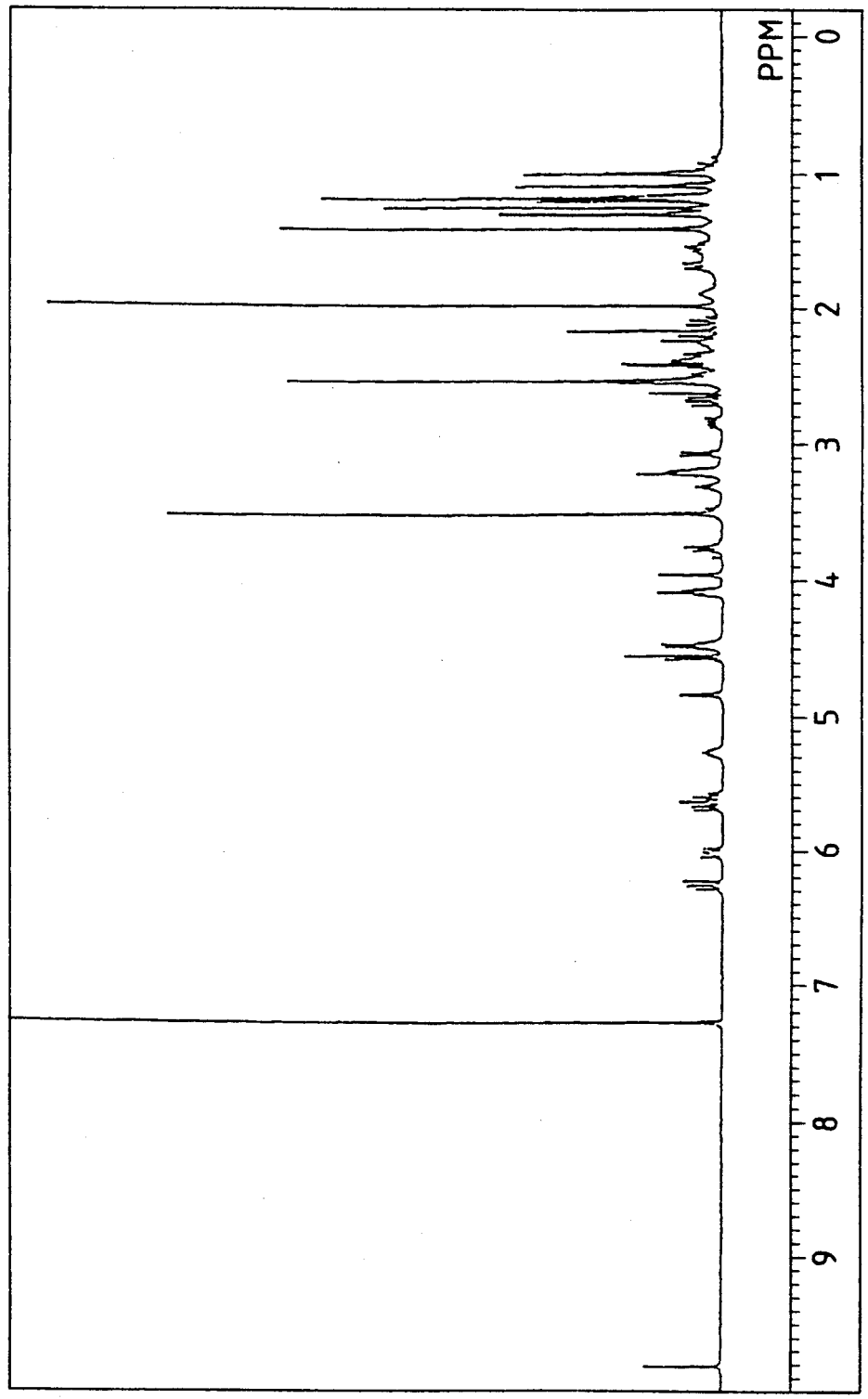
FIG. 7 is the 400 MHz $^1$H-NMR spectrum of the compound of formula (IV) in a deuterated chloroform solution.
Figure 8:
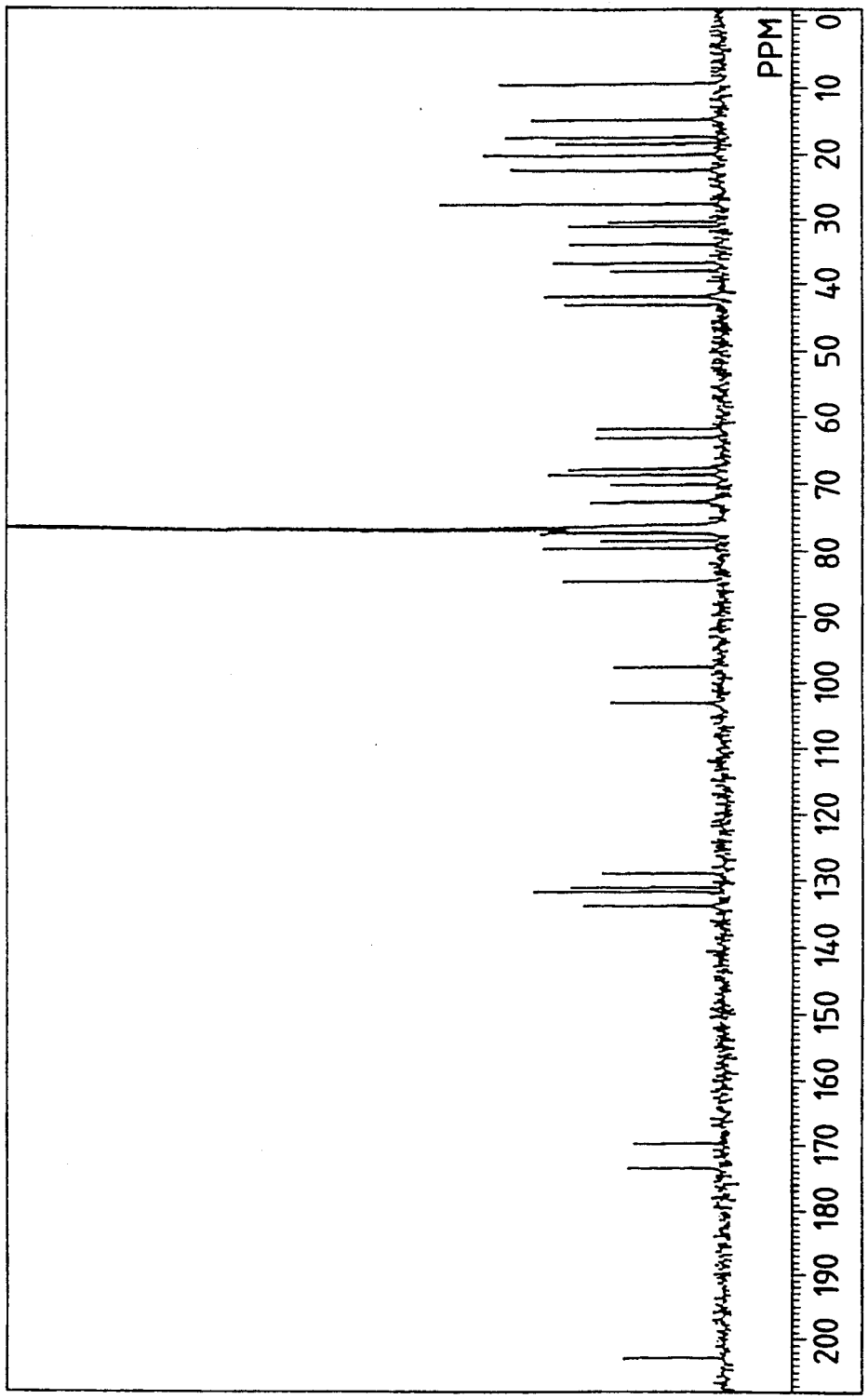
FIG. 8 is the 100 MHz $^{13}$C-NMR spectrum of the compound of formula (IV) in a deuterated chloroform solution.
Figure 9:
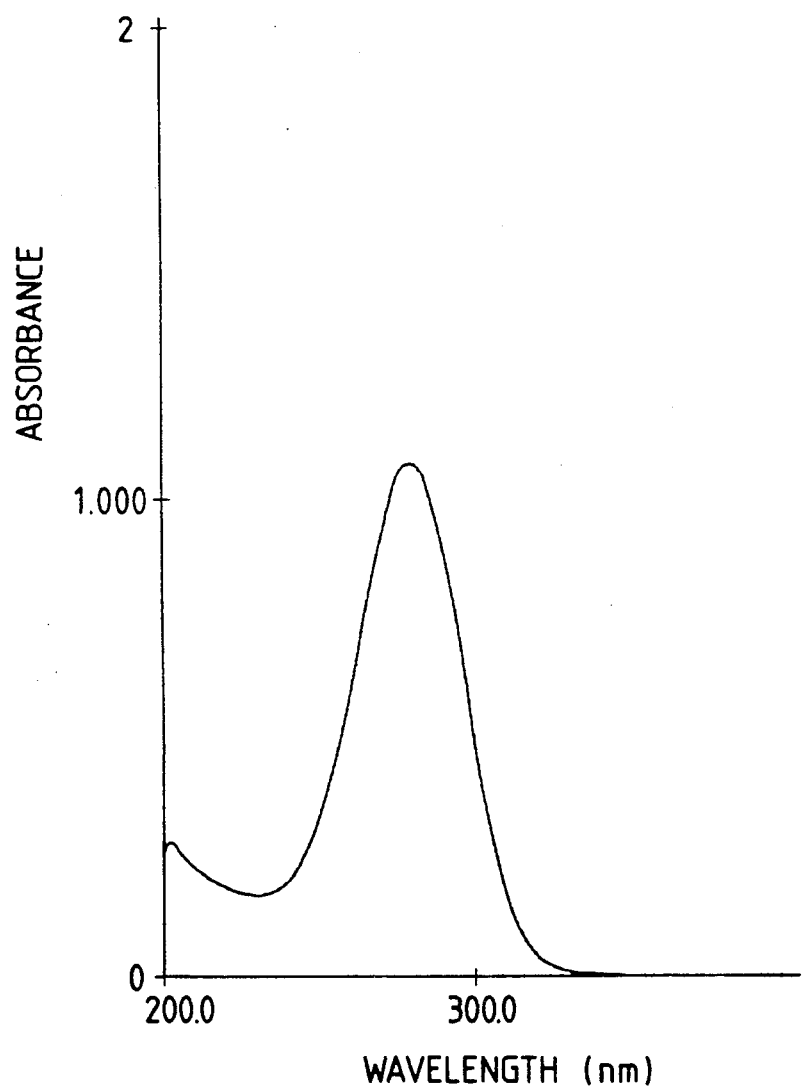
FIG. 9 is the UV absorption spectrum of the compound of formula (V) in methanol (50 μg/ml).
Figure 10:
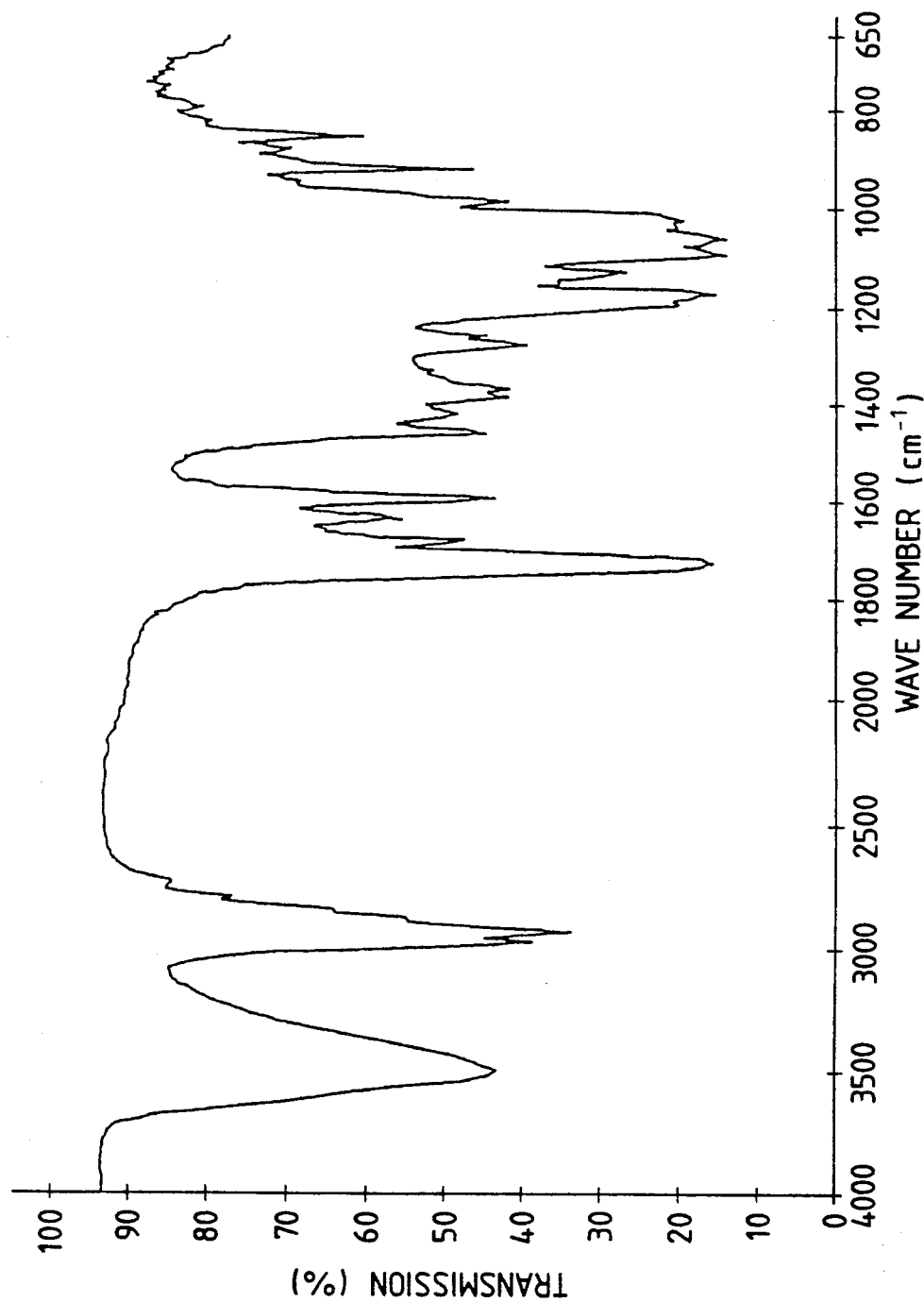
FIG. 10 is the IR absorption spectrum of the compound of formula (V) in potassium bromide tablets.
Figure 11:
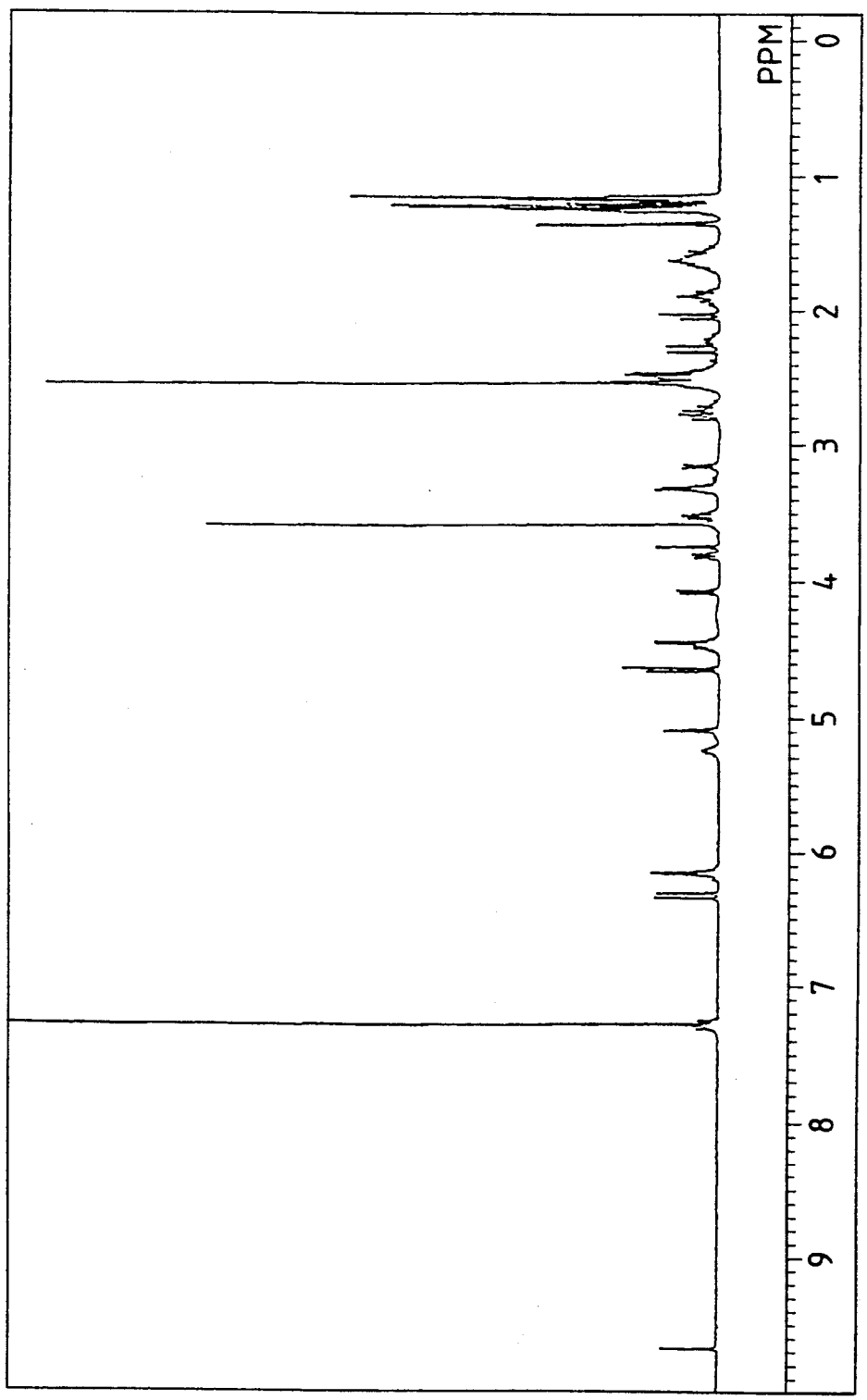
FIG. 11 is the 400 MHz $^1$H-NMR spectrum of the compound of formula (V) in a deuterated chloroform solution.
Figure 12:
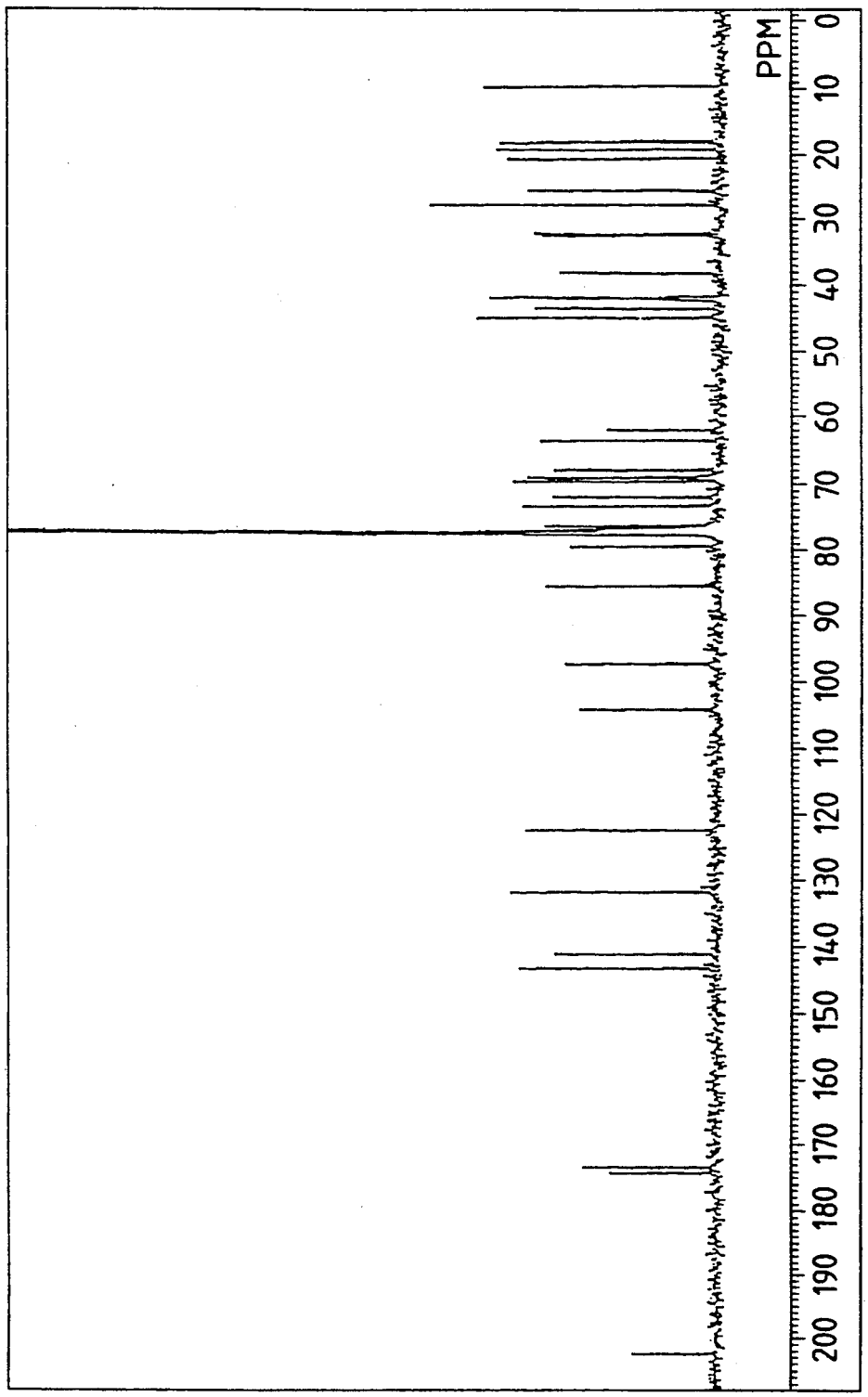
FIG. 12 is the 100 MHz $^{13}$C-NMR spectrum of the compound of formula (V) in a deuterated chloroform solution.

The first embodiment of the present invention is a method of producing a 3-deacylated derivative represented by formula (II) or (III) which comprises adding a macrolide antibiotic represented by formula (I) to a culture broth of a fungus strain, a buffer solution containing washed cells of said strain or a solution of an enzyme produced by the strain and collecting the target compound from the culture medium or the reaction mixture.

Examples of the fungus to be used in the present invention include strains PF1083 and PF1086 isolated from the soil in Sanada-cho, Nagano, Japan.

1. Mycological characteristics of strain PF1083

(1) Growth state

When incubated on a potato dextrose agar medium or a malt extract agar medium at 25° C. for 7 days, gently-sloping lanata colonies having a diameter of 22–25 mm are formed. These colonies are pale brown at the initial stage and then turn into dark brown within 2 to 3 weeks. The reverse surface of the colonies are dark orange at the initial stage and then turns into dark brown to black. When incubated on an oatmeal agar medium at 25° C. for 7 days, flat colonies having a diameter of 20–23 mm are formed. These colonies have an olive color at the initial stage and then turn into dark brown within 2 to 3 weeks. The reverse surface has the same color as the top surface. When incubated at 37° C., this strain grows only slowly in any medium and colonies having a diameter of 8–10 mm are formed within 7 days.

(2) Morphology

Hyphae are an olive color and ranges from 2 to 4 μm in width. They have septa and are branched. Phialaides ranges from 5 to 10 μm in length, from 2 to 3 μm and from 1 to 2 μm in width respectively at the base and at the tip. They are an olive color and a pot-form with a collar at the tip. Conidia are 1.5–2.5×3.5–6.0 μm in size and have a smooth surface. They are colorless ellipsoid.

Based on the above-mentioned mycological characteristics, this strain seemingly belongs to the genus Phialophora of Fungi Imperfecti. Thus it has been named Phialophora sp. PF1083 and deposited with Fermentation Research Institute of Agency of Industrial Science and Technology of 1-3, Higashi 1-chome, Tsukuba-shi, Ibaraki 305 Japan under accession number FERM BP-3960.

2. Mycological characteristics of strain PF1086

(1) Growth state

This strain grows well on an oatmeal agar medium. After incubating at 25° C. for 21 days, down-like colonies having a diameter of 65–75 mm are formed. These colonies are white at the initial stage and then turn into gray. A number of black cleistothecia are formed in the hypha layer. The reverse surface and the agar show a dark red color. When incubated on a potato-carrot agar medium at 25° C. for 21 days, white, down-like like colonies having a diameter of 45–55 mm are formed. A number of black cleistothecia are formed in the mycelium. The reverse surface and the agar show a reddish brown color. This strain never grows in any medium at 37° C.

(2) Morphology

Cleistothecia either scatter or loosely gather together. They are sub-spherical and have a diameter of from 250 to 400 μm (up to 800 μm in some case), a black color and smooth surface. Asci are double-walled, having 8 spores and in the form of clubs of 110–140×12–15 μm in size. The intermediate part is the most thickest while the base has a hook-like structure. The length of stalks ranges from 12 to 30 μm. A number of pseudoparaphysis, which are in the form of colorless hyphae of 2 to 3 μm in diameter and have septa, are present together with the asci. Ascospores, which are arranged in parallel in the asci, are cylindrical (27–33×5–7 μm) and have smooth walls. Four cells form a sectional septum which is somewhat compressed. These ascospores are colorless at the initial stage but turn into dark brown as the maturation proceeds. They are easily separated into individual cells. Cell pieces at the both ends are conical and somewhat longer than those in the intermediate part. Some cells show vertical or inclined germ slits. No conidial generation is formed.

Based on the above-mentioned mycological characteristics, this strain seemingly belongs to the genus Preussia of Loculoascomycetes. Thus it has been named Preussia sp. PF1086 and deposited with Fermentation Research Institute of Agency of Industrial Science and Technology under the accession number FERM BP-3961.

The above-mentioned strains PF1083 and PF1086 are liable to change in characteristics as usually observed with other fungi. Any spontaneous or induced mutant, zygote or recombinant of the strains PF1083 or PF1086 is usable in the present invention so long as it has a 3-deacylation activity on a 16-membered macrolide antibiotic. 3. Method of producing 3-deacylated derivative of 16-membered macrolide antibiotic The above-mentioned microorganism is first incubated in a liquid medium to prepare a seed culture. Then the seed culture thus obtained is added in a medium containing, for example, a carbon source and a nitrogen source together with a 16-membered macrolide antibiotic to give a cell concentration of 20 to 30% (packed volume). Alternatively, washed cells of said microorganism, which has been incubated, are dispersed in an appropriate buffer solution and then stirred together with a 16-membered macrolide antibiotic.

The washed cell dispersion can be prepared as follows. The microorganism is incubated in a medium for 1 to 2 days and the cells are collected by centrifugation. The resulting cells are washed with a buffer solution and recovered by centrifugation. The collected cells are dispersed in the same buffer solution to give a cell concentration of 5 to 10% (packed volume). Usable as a buffer solution are 1M Tris-hydrochloride buffer (pH 7.0–9.0) and 1M phosphate buffer (pH 5.0–7.0).

Although the 16-membered macrolide antibiotic may be added at any stage during the cultivation in a production medium, it is preferably added prior to the former logarithmic growth stage. In view of the conversion efficiency, the amount of the substrate to be added usually ranges from 0.1 to 2 mg/ml.

Any of known nutrient sources conventionally used for cultivation of fungi can be employed. Usable as a carbon source are glucose, sucrose, maltose syrup, dextrin, starch, molasses and animal and vegetable fats and oils. Usable as a nitrogen source are soybean flour, wheat germ, corn steep liquor, cotton seed cake, meat extract, peptone, yeast extract, ammonium sulfate, sodium nitrate and urea. The medium may contain inorganic salts capable of forming ions such as sodium, potassium, calcium, magnesium, cobalt, chlorine, phosphoric acid and sulfuric acid, if needed. Examples of the inorganic salts include sodium chloride, potassium chloride, calcium chloride, magnesium sulfate, cobalt chloride, dipotassium hydrogenphosphate and the like. Further, organic and inorganic substances capable of promoting the growth of the microorganism and accelerating the conversion of the substrate may be appropriately added to the medium. Usable as such organic substances are glutamic acid, aspartic acid, adenine, uracil, inositol, vitamin $B_{12}$ and the like. Examples of the inorganic substances include sodium chloride, potassium chloride, magnesium sulfage, cobalt chloride, dipotassium hydrogen-phosphate and the like.

The cultivation may be effected under aerobic conditions with submerged culture being particularly preferred. The incubation temperature may range from 24 to 30° C. The incubation is carried out mostly at around 26° C. The conversion rate of the substance may vary depending on the employed medium and incubation conditions. In the case of shaken culture or tank culture, the accumulation of the conversion product in the medium reaches the maximum level after 3- to 10-day incubation. When the accumulation of the conversion product in the medium reaches the maximum level, the incubation is ceased and the target substance is isolated and purified from the medium. When a washed cell dispersion is used, the incubation may be carried out at 24 to 28° C. for 12 to 48 hours.

The target conversion product may be obtained from the above-mentioned medium in the following manner. After the completion of the incubation, the cells are filtered off and the filtrate is made alkaline, for example, adjusted to pH 9.0 with 1N sodium hydroxide. Then it is extracted with an organic solvent immiscible with water such as butanol and ethyl acetate. Thus the conversion product is extracted into the organic solvent layer. For further purification, it is preferably to apply the conversion product thus extracted to chromatography using an adsorbent such as silica gel (Wako Gel C-300, manufactured by Wako Pure Chemical Industries) or alumina or a carrier such as ODS (Cosmosil, manufactured by Nakalai Tesque), Sephadex LH-20 (manufactured by Pharmacia) or Toyopearl HW-40 (manufactured by Tosoh Corp.). In order to purify a small amount of the target compound, preparative TLC (MERCK Art. 5744, manufactured by Merck Inc.) may be suitably employed. It is preferable to purify the conversion product by silica gel or almina chromatography followed by gel filtration using Sephadex LH20 or Toyopearl HW-40. The desired products in the eluate fractions can be detected by thin layer chromatography to compare an Rf value of the sample with that of a standard product or bioassay using Micrococcus lutes ATCC 9341.

The conversion product thus obtained may be separated in a free form. When a solution containing this conversion product or a concentrate thereof is treated with a pharmaceutically acceptable inorganic acid or organic acid at some stage during the above-mentioned procedure including extraction, separation and purification, the conversion product is separated in the form of the corresponding salt. Alternatively, a salt of the product thus obtained may be converted into a free form in a conventional manner. Further, the conversion product obtained in a free form may be converted into a salt with the use of a pharmaceutically acceptable inorganic or organic salt. The present invention involves not only the conversion products in a free form but also salts thereof. Examples of the pharmaceutically acceptable inorganic acid include hydrochloric acid, sulfuric acid, nitric acid, phosphoric acid. Examples of the pharmaceutically acceptable organic acid include acetic acid, stearic acid, malic acid and succinic acid.

The second embodiment of the present invention is novel macrolide antibiotics 3″-O-acetyl-3-depropionylneoisomidecamycin of formula (III), 3″-O-acetylleucomycin A$_7$ of formula (IV) and 9-dehydroleucomycin A$_7$ of formula (V) as well as pharmaceutically acceptable salts thereof. The physicochemical and biological properties of these antibiotics according to the present invention are as follows.

1. Physicochemical properties of 3″-O-acetyl-3-depropionylneoisomidecamycin (1) Color and appearance: white powder.
(2) Molecular formula: $C_{40}H_{65}NO_{15}$.
(3) Mass spectrum (SI-MS): m/z 800 (M+1)$^+$.
(4) Specific rotation: $[\alpha]_D^{23} = -63°$ (c 0.34, CHCl$_3$).
(5) UV absorption spectrum:
λmax nm(ξ) [MeOH]: 227 (3900), 278 (310).
(6) IR absorption spectrum:
(KBr cm$^{-1}$): 3460, 2980, 2930, 2840, 2780, 1735, 1460, 1435, 1380, 1370, 1280, 1255, 1180, 1160, 1135, 1090, 1070, 1060, 1040, 980, 915, 880, 845, 815.
(7) $^1$H NMR spectrum (400 MHz, CDCl$_3$).
δ(ppm): 2.39 (dd, 2-H), 2.68 (dd, 2-H), 3.88 (br d, 3-H), 3.21 (dd, 4-H), 3.55 (s, 4-OCH$_3$), 3.96 (dd, 5-H), 2.19 (m, 6-H), 1.10 (m, 7-H), 1.50 (ddd, 7-H), 2.14 (m, 8-H), 5.50 (dd, 9-H), 5.60 (dd, 10-H), 4.53 (br dd, 11-H), 5.63 (m, 12-H), 5.64 (m, 13-H), 2.29 (ddd, 14-H), 2.46 (m, 14-H), 5.15 (ddq, 15-H), 1.31 (d, 16-H$_3$), 2.35 (dd, 17-H), 2.92 (br dd, 17-H), 9.76 (br s, 18-H), 1.04 (d, 19-H$_3$), 4.46 (d, 1′-H), 3.32 (dd, 2′-H), 2.37 (m, 3′-H), 3.23 (m, 4′-H), 3.22 (m, 5′-H), 1.17 (br d, 6′-H$_3$), 2.56 (s, 3′-N(CH$_3$)$_2$), 4.88 (br d, 1″-H), 1.71 (dd, 2″-Hax), 3.23 (br d, 2″-Heq), 4.59 (d, 4″-H), 4.50 (m, 5″-H), 1.10 (d, 6″-H$_3$), 1.42 (s, 7″-H$_3$), 2.01 (s, 3″-OCOCH$_3$), 2.43 (M, 4″-OCOCH$_2$CH$_3$), 1.20 (t, 4″-OCOCH$_2$CH$_3$).
(8) $^{13}$C NMR spectrum (100 MHz, CDCl$_3$).
δ(ppm): (171.95 (s, C-1), 39.44 (t, C-2), 68.53 (d, C-3), 85.91 (d, C-4), 61.81 (q, 4-OCH$_3$), 79.83 (d, C-5), 31.02 (d, C-6), 35.89 (t, C-7), 33.03 (d, C-8), 136.25 (d, C-9), 131.9 (d, C-10), 72.87 (d, C-11), 133.10 (d, C-12), 129.68 (d, c-13), 39.82 (t, C-14), 69.94 (d, C-15), 20.26 (q, C-16), 44.01 (t, C-17), 202.95 (d, C-18), 21.44 (q, C-19), 103.68 (d, C-1′), 70.46 (d, C-2′), 69.20 (d, C-3′), 80.09 (d, C-4′), 73.18 (d, C-5′), 18.36 (q, C-6′), 41.49 (q, 3′-N(CH$_3$)$_2$), 98.43 (d, C-1″), 36.59 (t, C-2″), 77.92 (s, C-3″), 77.60 (d, C-4″), 63.41 (d, C-5″), 17.31 (q, C-6″), 22.25 (q, C-7″), 170.40 (s, 3″-OCOCH$_3$), 22.50 (q, 3″-OCOCH$_3$), 174.07 (s, 4″-OCOCH$_2$CH$_3$), 27.58 (t, 4″-OCOCH$_2$CH$_3$), 9.28 (q, 4″-OCOCH$_2$CH$_3$).
(9) Solubility: soluble in chloroform, acetone, ethyl acetate, methanol and acidic water and insoluble in neutral and alkaline water.
(10) Basic, acidic or neutral: basic substance.

3. Physicochemical properties of 3″-acetylleucomycin A$_7$ (1) Color and appearance: white powder.
(2) Molecular formula: $C_{40}H_{65}NO_{15}$.
(3) Mass spectrum (SI-MS): m/z 800 (M+1)$^+$.
(4) Specific rotation: $[\alpha]_D^{23} = -69°$ (c 0.29, CHCl$_3$).
(5) UV absorption spectrum:
λmax nm (ε) [MeOH]: 230 (23300).
(6) IR absorption spectrum:
(KBr cm$^{-1}$): 3460, 2980, 2940, 2840, 2790, 1740, 1460, 1435, 1380, 1370, 1280, 1255, 1190, 1165, 1140, 1095, 1080, 1065, 1040, 1000, 960, 920, 880, 850, 820.
(7) $^1$H NMR spectrum (400 MHz, CDCl$_3$).
δ(ppm): 2.24 (dd, 2-H), 2.70 (dd, 2-H), 3.79 (br d, 3-H), 3.08 (br d, 4-H), 3.54 (s, 4-OCH$_3$), 4.10 (dd, 5-H), 2.28 (m, 6-H), 0.97 (ddd, 7-H), 1.56 (ddd, 7-H), 1.91 (m, 8-H), 4.12 (dd, 9-H), 5.69 (dd, 10-H), 6.27 (dd, 11-H), 6.03 (br dd, 12-H), 5.62 (ddd, 13-H), 2.12 (ddd, 14-H), 2.51 (m, 14-H), 5.30 (ddq, 15-H), 1.31 (d, 16-H$_3$), 2.37 (dd, 17-H), 2.87 (br dd, 17-H), 9.81 (br S, 18-H), 1.00 (d, 19-H$_3$), 4.50 (d, 1′-H), 3.34 (dd, 2′-H), 2.37 (m, 3′-H), 3.22 (m, 4′-H), 3.23 (m, 5′-H), 1.18 (br d, 6′-H$_3$), 2.55 (s, 3'-N(CH$_3$)$_2$), 4.87 (br d, 1"-H), 1.70 (dd, 2"-Hax), 3.22 (br d, 2"-Heq), 4.59 (d, 4"-H), 4.50 (m, 5"-H), 1.10 (d, 6"-H$_3$), 1.42 (s, 7"-H$_3$), 2.00 (s, 3"-OCOCH$_3$), 2.43 (m, 4"-OCOCH$_2$CH$_3$), 1.20 (t, 4"-OCOCH$_2$CH$_3$).

(8) $^{13}$C NMR spectrum (100 MHz, CDCl$_3$).

δ(ppm): 174.16* (s, C-1), 37.85 (t, C-2), 68.18 (d, C-3), 85.12 (d, C-4), 61.92 (q, 4-OCH$_3$), 79.02 (d, C-5), 30.30 (d, C-6), 30.98 (t, C-7), 33.73 (d, C-8), 73.05 (d, C-9), 129.70 (d, C-10), 134,51 (d, C-11), 132.43 (d, C-12), 131.78 (d, C-13), 41.84 (t, C-14), 69.04 (d, C-15), 20.12 (q, C-16), 42.93 (t, C-17), 202.74 (d, C-18), 14.71 (q, C-19), 103.74 (d, C-1'), 70.52 (d, C-2'), 69.20 (d, C-3'), 80.14 (d, C-4'), 73.22 (d, C-5'), 18.31 (q, C-6'), 41.52 (q, 3'-N(CH$_3$)$_2$), 98.41 (d, C-1"), 36.59 (t, C-2"), 77.92 (s, C-3"), 77.62 (d, C-4"), 63.39 (d, C-5"), 17.31 (q, C-6"), 22.26 (q, C-7"), 170.40 (s, 3"-OCOCH$_3$), 22.49 (q, 3"-OCOCH$_3$), 174.07* (s, 4"-OCOCH$_2$CH$_3$), 27.58 (t, 4"-OCOCH$_2$CH$_3$), 9.28 (q, 4"-OCOCH$_2$CH$_3$).

(9) Solubility: soluble in chloroform, acetone, ethyl acetate, methanol and acidic water and insoluble in neutral and alkaline water.

(10) Basic, acidic or neutral: basic substance.

3. Physicochemical properties of 9-dehydroleucomycin A$_7$
(1) Color and appearance: white powder.
(2) Molecular formula: C$_{38}$H$_{61}$NO$_{14}$.
(3) Mass spectrum (SI-MS): m/z 756 (M+1)$^+$.
(4) Specific rotation: [α]$_D^{23}$ = −27° (c 0.40, CHCl$_3$).
(5) UV absorption spectrum:
λmax nm (ε) [MeOH]: 280 (16300).
(6) IR absorption spectrum:
(KBr cm$^{-1}$): 3490, 2975, 2930, 2870, 2830, 2780, 2575, 1725, 1675, 1630, 1590, 1460, 1415, 1380, 1360, 1330, 1280, 1260, 1190, 1170, 1150, 1130, 1090, 1060, 1035, 1025, 985, 940, 920, 870, 850, 815, 790.
(7) $^1$H NMR spectrum (400 MHz, CDCl$_3$).

δ(ppm): 2.26 (br d, 2-H), 2.76 (dd, 2-H), 3.80 (br d, 3-H), 3.14 (br d, 4-H), 3.56 (s, 4-OCH$_3$), 4.06 (dd, 5-H), 1.90 (m, 6-H), 1.53 (ddd, 7-H), 1.64 (ddd, 7-H), 2.54 (m, 8-H), 6.32 (d, 10-H), 7.27 (dd, 11-H), 6.16 (m, 12-H), 6.16 m, 13-H), 2.20 (m, 14-H), 2.47 (m, 14-H), 5.23 (ddq, 15-H), 1.34 (d, 16-H$_3$), 2.49 (m, 17-H), 2.73 (ddd, 17-H), 9.68 (br d, 18-H), 1.21 (d, 19-H:), 4.43 (d, 1'-H), 3.50 (dd, 2'-H), 2.47 (m, 3'-H), 3.28 (m, 4'-H), 3.30 (m, 5'-H), 1.23 (br d, 6'-H$_3$), 2.51 (s, 3'-N(CH$_3$)$_2$), 5.08 (br d, 1"-H), 1.85 (dd, 2"-Hax), 2.02 (br d, 2"-Heq), 4.63 (d, 4"-H), 4.46 (dq, 5"-H), 1.14 (d, 6"-H$_3$), 1.12 (s, 7"-H:), 2.43 (dq, 4"-OCOCH$_2$CH$_3$), 2.46 (dq, 4"-OCOCH$_2$CH$_3$), 1.19 (t, 4"-OCOCH$_2$CH$_3$).

(8) $^{13}$C NMR spectrum (100 MHz, CDCl$_3$). (

δ(ppm): 173.50* (s, C-1), 38.06 (t, C-2), 67.72 (d, C-3), 85.39 (d, C-4), 61.89 (q, 4-OCH$_3$), 79.29 (d, C-5), 32.02 (d, C-6), 32.45 (t, C-7), 44.79 (d, C-8), 202.32 (s, C-9), 122.40 (d, C-10), 143.24 (d, C-11), 131.75 (d, C-12), 141.14 (d, C-13), 41.69 (t, C-14), 68.86 (d, C-15), 20.29 (q, C-16), 43.32 (t, C-17), 202.44 (d, C-18), 17.43 (q, C-19), 104.00 (d, C-1,), 71.67 (d, C-2'), 68.76 (d, C-3'), 76.08 (d, C-4'), 73.11 (d, C-5,), 18.83 (q, C-6'), 41.88 (q, 3'-N(CH$_3$)$_2$), 97.09 (d, C-1"), 41.64 (t, C-2"), 69.36 (s, C-3"), 77.00 (d, C-4"), 63.48 (d, C-5"), 17.74 (q, C-6"), 25.30 (q, C-7"), 174.39* (s, 4"-OCOCH$_2$CH$_3$), 27.59 (t, 4"-OCOCH$_2$CH$_3$), 9.32 (q, 4"-OCOCH$_2$CH$_3$)

(9) Solubility: soluble in chloroform, acetone, ethyl acetate, methanol and acidic water and insoluble in neutral and alkaline water.

(10) Basic, acidic or neutral: basic substance.

4. Biological activities

Table 1 shows the minimum inhibitory concentrations of 3"-O-acetyl-3-depropionylneoisomidecamycin, 3-O-acetylleucomycin A$_7$ and 9-dehydroleucomycin A$_7$ of the present invention on various bacteria.

TABLE 1

| Test strain | Minimum inhibitory concentration (μg/ml) | | |
|---|---|---|---|
| | (III)* | (IV)* | (V)* |
| *Staphylococcus aureus* 209P JC-1 | 0.20 | 0.10 | 0.10 |
| *Staphylococcus aureus* M133 | 0.39 | 0.78 | 0.39 |
| *Staphylocuccus aureus* M126 | >100 | >100 | >100 |
| *Staphylocuccus epidermidis* ATCC14990 | 0.39 | 0.39 | 0.39 |
| *Enterococcus hirae* ATCC8043 | 0.39 | 0.39 | 0.39 |
| *Enterococcus faecalis* W-73 | 0.78 | 0.78 | 0.78 |
| *Escherichia coli* W3630 RGN823 | 12.5 | 6.25 | 12.5 |
| *Escherichia coli* NIHJ JC-2 | >100 | >100 | >100 |
| *Escherichia coli* GN206 | 12.5 | 12.5 | 12.5 |
| *Klebsiella pneumoniae* PCI602 | >100 | >100 | >100 |
| *Proteus vulgaris* GN76 | >100 | >100 | >100 |
| *Pseudomonas aeruginosa* GN10362 | >100 | >100 | >100 |

*Note:
(III): the compound of formula (III)
(IV): the compound of formula (IV)
(V): the compound of formula (V)

As shown in Table 1, the compounds of the present invention exhibits antibiotic activity against certain kinds of bacteria.

The following examples are given to further illustrate the present invention. Since a method of producing a 3-deacylated derivative of a 16-membered macrolide antibiotic using a microorganism belonging to the genus Phialophora or a has been revealed, various approaches can be taken for the production of said substance using similar microorganisms. The following examples are not construed to limit the scope of the present invention. The present invention involves any method of production, concentration extraction and purification of the above-mentioned 3"-O-acetyl-3-depropionyl-neoisomidecamycin, 3"-O-acetylleucomycin A$_7$ and 9-dehydroleucomycin A$_7$ according to the characteristics thereof using known procedures as well as modifications of the methods employed in the examples.

EXAMPLE 1

Microbial conversion of midecamycin [in formula (I), R$^1$ and R$^5$ each represents a propionyl group, R$^2$ and R$^4$ each represents a hydrogen atom, and R$^3$ is a hydroxyl group] into leucomycin A$_7$ in formula (II), R$^1$ and R$^3$ each represents a hydrogen atom, R$^2$ is a hydroxyl group and R$^4$ is a propionyl group]:

A medium comprising 2.0% starch, 1.0% glucose, 0.6% wheat germ, 0.5% polypeptone, 0.3% yeast extract powder, 0.2% soybean flour and 0.2% calcium carbonate was used as a seed medium. A medium comprising 2.0% glucose, 1.25% soybean flour, 1.0% starch, 0.8% wheat germ, 0.125% sodium chloride and 0.15% calcium carbonate was employed as a production medium. Prior to sterilization, the pH value of each medium was adjusted to 7.0.

20 ml of the above-mentioned seed medium was charged into a 100-ml Erlenmeyer flask and sterilized at 120° C. for 30 minutes. Then a platinum loopful of a slant agar culture of the strain Phialophora sp. PF1083 (FERM BP-3960) was inoculated into this medium and incubated at 26° C. for 2 days with shaking to thereby give a seed culture. Next, thirty 500-ml Erlenmeyer flasks, each containing 100 ml of the above-mentioned production medium, were sterilized at 120° C. for 30 minutes. Midecamycin was added to each flask to a concentration of 100 µg/ml and then 5 ml portions of the above-mentioned seed culture were inoculated therein followed by incubation at 26° C. for 7 days with shaking. After the completion of the incubation, diatomaceous earth was added to the culture as a filter aid and the incubation medium was filtered to thereby obtain 2 l of a filtrate. The filtrate was adjusted to pH 9 with 1N sodium hydroxide and then extracted with 2 l of ethyl acetate. The ethyl acetate layer was concentrated to dryness to obtain 151 mg of an oily substance. Then this oily substance was placed on the top of a column packed with 15 g of silica gel and chromatography was carried out using chloroform/methanol (50 : 1 by volume) as a developing solvent. The eluate was collected in fractions (10 g). Fractions No. 20 to No. 23 which had been confirmed to contain the starting material by thin layer chromatography were concentrated to dryness and the crude powder thus obtained was dissolved in 1 ml of methanol and the resulting methanol solution was applied to a column packed with Sephadex LH-20 (100 ml) which had been equilibrated with methanol. Elution was carried out with methanol and active fractions were concentrated to dryness to obtain 15.1 mg of midecamycin. Next, fractions No. 25 to No. 35 which had been confirmed to contain the converted product by thin layer chromatography were concentrated to dryness and the crude powder thus obtained was purified using 200 ml of Sephadex LH-20 in the same manner as described above. Thus 101.1 mg of leucomycin $A_7$ was obtained.

Physical data of isolated leucomycin $A_7$ (1) Mass spectrum (SI-MS): m/z 758 (M+1)+. (2) Specific rotation: $[\alpha]_D^{23} = -59°$ (c 0.38, CHCl$_3$).

(3) $^1$H NMR spectrum (400 MHz, CDCl$_3$).

δ(ppm): 2.25 (dd, 2-H), 2.69 (dd, 2-H), 3.79 (br d, 3-H), 3.07 (br d, 4-H), 3.51 (s, 4-OCH$_3$), 4.10 (dd, 5-H), 2.30 (m, 6-H), 0.96 (ddd, 7-H), 1.50 (ddd, 7-H), 1.90 (m, 8-H), 4.12 (dd, 9-H), 5.69 (dd, 10-H), 6.26 (dd, 11-H), 6.02 (br dd, 12-H), 5.62 (ddd, 13-H), 2.11 (ddd, 14-H), 2.51 (m, 14-H), 5.29 (ddq, 15-H), 1.31 (d, 16-H:), 2.37 (dd, 17-H), 2.84 (ddd, 17-H), 9.79 (br s, 18-H), 1.01 (d, 19-H$_3$), 4.48 (d, 1'-H), 3.52 (dd, 2'-H), 2.46 (m, 3'-H), 3.28 (m, 4'-H), 3.29 (m, 5'-H), 1.23 (br d, 6'-H$_3$), 2.51 (s, 3'-N(CH$_3$)$_2$), 5.07 (br d, 1''-H), 1.84 (dd, 2''-Hax), 2.01 (br d, 2''-Heq), 4.62 (d, 4''-H), 4.45 (m, 5''-H), 1.13 (d, 6''-H$_3$), 1.12 (s, 7''-Hi), 2.42 (dq, 4''-OCOCH$_2$CH$_3$), 2.46 (dq, 4''-OCOCH$_2$CH$_3$), 1.18 (t, 4''-OCOCH$_2$CH$_3$).

(4) $^{13}$C NMR spectrum (100 MHz, CDCl$_3$).

δ(ppm): 174.05* (s, C-1), 37.75 (t, C-2), 68.18 (d, C-3), 85.18 (d, C-4), 61.75 (q, 4-OCH$_3$), 79.02 (d, C-5), 30.41 (d, C-6), 30.94 (t, C-7), 33.77 (d, C-8), 73.01 (d, C-9), 129.73 (d, C-10), 134.41 (d, C-11), 132.35 (d, C-12), 131.78 (d, C-13), 41.79 (t, C-14), 69.09 (d, C-15), 20.08 (q, C-16), 42.95 (t, C-17), 202.63 (d, C-18), 14.79 (q, C-19), 103.82 (d, C-1'), 71.62 (d, C-2'), 68.70 (d, C-3'), 75.88 (d, C-4'), 73.01 (d, C-5'), 18.82 (q, C-6'), 41.89 (q, 3'-N(CH$_3$)$_2$), 96.93 (d, C-1''), 41.64 (t, C-2''), 69.35 (s, C-3''), 77.12 (d, C-4''), 63.43 (d, C-5''), 17.71 (q, C-6''), 25.24 (q, C-7''), 174.39* (s, 4''-OCOCH$_2$CH$_3$), 27.55 (t, 4''-OCOCH$_2$CH$_3$), 9.28 (q, 4''-OCOCH$_2$CH$_3$).

The seed and production media employed in the following Examples 2 to 7 were produced in the same manner as in Example 1.

EXAMPLE 2

Microbial conversion of midecamycin A$_2$ [in formula (I), R$^1$ is a propionyl group, R$^2$ and R$^4$ each represents a hydrogen atom, R$^3$ is a hydroxyl group and R: is a butyryl group] into leucomycin A$_5$ [in formula (II), R$^1$ and R$^3$ each represents a hydrogen atom, R$^2$ is a hydroxyl group and R$^4$ is a butyryl group]:

Five 500-ml Erlenmeyer flasks, each containing 100 ml of the production medium, were sterilized at 120° C. for 30 minutes. Midecamycin A$_2$ was added to each flask to a concentration of 100 µg/ml and 5 ml portions of the seed culture were inoculated therein followed by incubation at 26° C. for 7 days with shaking. After the completion of the incubation, diatomaceous earth was added as a filter aid and the incubation medium was filtered to thereby obtain 350 ml of a filtrate. The filtrate was adjusted to pH 9 and then extracted with 350 ml of ethyl acetate. After concentrating the ethyl acetate layer to dryness, 41.0 mg of an oily substance was obtained. Then this oily substance was purified with preparative TLC (development system: chloroform/methanol, 10: 1 by volume) and two active components thus obtained were separately subjected to gel filtration using 40 ml of Sephadex LH-20. Thus 17.3 mg of leucomycin A$_5$ and 10.5 mg of midecamycin Az were recovered.

Physical data of isolated leucomycin A.

(1) Mass spectrum (SI-MS): m/z 772 (M+1)+.
(2) Specific rotation: $[\alpha]_D^{23} = -54°$ (c 0.60, CHCl$_3$).
(3) $^1$H NMR spectrum (400 MHz CDCl$_3$).

δ(ppm): 2.25 (dd, 2-H), 2.70 (dd, 2-H), 3.80 (br d, 3-H), 3.08 (br d, 4-H), 3.51 (s, 4-OCH$_3$), 4.11 (dd, 5-H), 2.30 (m, 6-H), 0.96 (ddd, 7-H), 1.51 (ddd, 7-H), 1.91 (m, 8-H), 4.12 (dd, 9-H), 5.69 (dd, 10-H), 6.27 (dd, 11-H), 6.03 (br dd, 12-H), 5.63 (ddd, 13-H), 2.12 (ddd, 14-H), 2.53 (m, 14-H), 5.30 (ddq, 15-H), 1.31 (d, 16-H$_3$), 2.38 (dd, 17-H), 2.84 (ddd, 17-H), 9.80 (br s, 18-H), 1.02 (d, 19-H$_3$), 4.48 (d, 1'-H), 3.53 (dd, 2'-H), 2.47 (m, 3'-H), 3.28 (m, 4'-H), 3.30 (m, 5'-H), 1.23 (br d, 6'-H$_3$), 2.51 (s, 3'-N(CH$_3$)$_2$), 5.08 (br d, 1''-H), 1.85 (dd, 2''-Hax), 2.02 (br d, 2''-Heq), 4.63 (d, 4''-H), 4.46 (dq, 5''-H), 1.14 (d, 6''-H$_3$), 1.12 (s, 7''-H$_3$), 2.40 (m, 4''-OCOCH$_2$CH$_2$CH$_3$), 1.70 (tq, 4''-OCOCH$_2$CH$_2$CH$_3$), 0.97 (t, OCOCH$_2$CH$_2$CH$_3$)

(4) $^{13}$C NMR spectrum (100 MHz, CDCl$_3$).

δ(ppm) 174.11* (s, C-1), 37.76 (t, C-2), 68.20 (d, C-3), 85.22 (d, C-4), 61.78 (q, 4-OCH$_3$), 79.06 (d, C-5), 30.44 (d, C-6), 30.99 (t, C-7), 33.77 (d, C-8), 73.06 (d, C-9), 129.72 (d, C-10), 134.51 (d, C-11), 132.36 (d, C-12), 131.86 (d, C-13), 41.84 (t, C-14), 69.11 (d, C-15), 20.10 (q, C-16), 42.99 (t, C-17), 202.56 (d, C-18), 14.80 (q, C-19), 103.85 (d, C-1,), 71.66 (d, C-2'), 68.74 (d, C-3'), 75.98 (d, C-4'), 73.06 (d, C-5'), 18.85 (q, C-6'), 41.93 (q, 3'-N(CH$_3$)$_2$), 97.02 (d, C-1''), 41.69 (t, C-2''), 69.35 (s, C-3''), 77.08 (d, C-4''), 63.47 (d, C-5''), 17.78 (q, C-6''), 25.31 (q, C-7''), 173.54* (s, 4''-OCOCH$_2$CH$_2$CH$_3$), 36.17 (t, 4''-OCOCH$_2$CH$_2$CH$_3$), 18.55 (t, 4''-OCOCH$_2$CH$_2$CH$_3$), 13.69 (q, 4''-OCOCH$_2$CH$_2$CH$_3$).

EXAMPLE 3

Microbial conversion of midecamycin a$_3$ [in formula (I), R$^1$ and R$^5$ each represents a propionyl group, R$^2$ and R$^3$ form a carbonyl group together with the carbon atom to which they are bound, and R$^4$ is a hydrogen atom] into 9-dehydroleucomycin A$_7$ [formula (V)]:

Five 500-ml Erlenmeyer flasks, each containing 100 ml of the production medium, were sterilized at 120° C. for 30 minutes. Midecamycin A$_3$ was added to each flask to a concentration of 100 μg/ml and 5 ml portions of the seed culture were inoculated therein followed by incubation at 26° C. for 7 days with shaking. After the completion of the incubation, diatomaceous earth was added as a filter aid and the incubation medium was filtered to thereby obtain 380 ml of a filtrate. The filtrate was adjusted to pH 9 and then extracted with 380 ml of ethyl acetate. The ethyl acetate layer was concentrated to dryness to obtain 32.0 mg of an oily substance. Then this oily substance was purified with preparative TLC (development system: chloroform/methanol, 10 : 1 by volume) and two active components thus obtained were separately subjected to gel filtration using 40 ml of Sephadex LH-20. Thus 2.9 mg of 9-dehydroleucomycin A$_7$ and 19.8 mg of midecamycin A$_3$ were recovered.

EXAMPLE 4

Microbial conversion of M$_1$ [in formula (I), R$^1$ is a propionyl group, R$^2$, R$^4$ and R$^5$ each represents a hydrogen atom and R$^3$ is a hydroxyl group] into leucomycin V [in formula (II), R$^1$, R$^3$ and R$^4$ each represents a hydrogen atom and R$^2$ is a hydroxyl group]:

Ten 500-ml Erlenmeyer flasks, each containing 100 ml of the production medium, were sterilized at 120° C. for 30 minutes. M$_1$ was added to each flask to a concentration of 100 μg/ml and 5 ml portions of the seed culture were inoculated therein followed by incubation at 26° C. for 7 days with shaking. After the completion of the incubation, diatomaceous earth was added as a filter aid and the incubation medium was filtered to thereby obtain 710 ml of a filtrate. The filtrate was adjusted to pH 9 and then extracted with 710 ml of ethyl acetate. The ethyl acetate layer was concentrated to dryness to obtain 71.5 mg of an oily substance. Then this oily substance was purified with preparative TLC (development system: chloroform/methanol, 5 : 1 by volume) and two active components thus obtained were separately subjected to gel filtration using 40 ml of Sephadex LH-20. Thus 20.2 mg of leucomycin V and 25.5 mg of M$_1$ were recovered.

Physical data of isolated leucomycin V (1) Mass spectrum (SI-MS): m/z 702 (M+1)$^+$.
(2) Specific rotation: $[\alpha]_D^{23} = -54°$ (c 0.41, CHCl$_3$).
(3) $^1$H NMR spectrum (400 MHz, CDCl$_3$).

δ(ppm): 2.25 (dd, 2-H), 2.69 (dd, 2-H), 3.80 (br d, 3-H), 3.08 (dd, 4-H), 3.51 (s, 4-OCH$_3$), 4.11 (dd, 5-H), 2.30 (m, 6-H), 0.97 (ddd, 7-H), 1.50 (ddd, 7-H), 1.91 (m, 8-H), 4.12 (dd, 9-H), 5.69 (dd, 10-H), 6.27 (dd, 11-H), 6.03 (br dd, 12-H), 5.62 (ddd, 13-H), 2.12 (ddd, 14-H), 2.52 (m, 14-H), 5.29 (ddq, 15-H), 1.31 (d, 16-H:), 2.38 (dd, 17-H), 2.84 (ddd, 17-H), 9.80 (br s, 18-H), 1.02 (d, 19-H:), 4.47 (d, 1,-H), 3.54 (dd, 2'-H), 2.46 (m, 3'-H), 3.27 (m, 4'-H), 3.28 (m, 5'-H), 1.24 (br d, 6'-H:), 2.49 (s, 3-N(CH$_3$)$_2$), 5.08 (br d, 1''-H), 1.76 (dd, 2''-Hax), 2.04 (br d, 2''-Heq), 2.95 (d, 4''-H), 4.07 (m, 5''-H), 1.30 (d, 6''-H$_3$), 1.24 (s, 7''-H$_3$).

(4) $^{13}$C NMR spectrum (100 MHz, CDCl$_3$).

δ(ppm): 174.08 (s, C-1), 37.78 (t, C-2), 68.20 (d, C-3), 85.23 (d, C-4), 61.75 (q, 4-OCH$_3$), 79.11 (d, C-5), 30.45 (d, C-6), 30.99 (t, C-7), 33.78 (d, C-8), 73.05* (d, C-9), 129.74 (d, C-10), 134.48 (d, C-11), 132.36 (d, C-12), 131.85 (d, C-13), 41.83 (t, C-14), 69.12 (d, C-15), 20.10 (q, C-16), 43.00 (t, C-17), 202.55 (d, C-18), 14.81 (q, C-19), 103.90 (d, C-1'), 71.78 (d, C-2'), 68.81 (d, C-3'), 74.99 (d, C-4'), 73.14* (d, C-5'), 19.05 (q, C-6'), 42.00 (q, 3'-N(CH$_3$)$_2$), 96.46 (d, C-1''), 40.91 (t, C-2''), 69.43 (s, C-6''), 76.43 (d, C-4''), 66.04 (d, C-5''), 18.25 (q, C-6'), 25.39 (q, C-7'').

EXAMPLE 5

Microbial conversion of josamycin [in formula (I), R$^1$ is an acetyl group, R$^2$ and R$^4$ each represents a hydrogen atom, R$^3$ is a hydroxyl group and R$^5$ is an isovaleryl group] into leucomycin A$_1$ [in formula (II), R$^1$ and R$^3$ each represents a hydrogen atom, R$^2$ is a hydroxyl group and R$^4$ is an isovaleryl group]:

Five 500-ml Erlenmeyer flasks, each containing 100 ml of the production medium, were sterilized at 120° C. for 30 minutes. Josamycin was added to each flask to a concentration of 100 μg/ml and 5 ml portions of the seed culture were inoculated therein followed by incubation at 26° C. for 10 days with shaking. After the completion of the incubation, diatomaceous earth was added as a filter aid and the incubation medium was filtered to thereby obtain 340 ml of a filtrate. The filtrate was adjusted to pH 9 and then extracted with 340 ml of ethyl acetate. The ethyl acetate layer was concentrated to dryness to obtain 33.2 mg of an oily substance. Then this oily substance was purified with preparative TLC (development system: chloroform/methanol, 10 : 1 by volume) and two active components thus obtained were separately subjected to gel filtration using 40 ml of Sephadex LH-20. Thus 4.5 mg of leucomycin A$_1$ and 12.2 mg of josamycin were recovered.

Physical data of isolated leucomycin A$_1$ (1) Mass spectrum (SI-MS): m/z 786 (M+1)$^+$.
(2) Specific rotation : $[\alpha]_D^{23} = -63°$ (c 0.31, CHCl$_3$).
(3) $^1$H NMR spectrum (400 MHz, CDCl$_3$).

δ(ppm): 2.25 (dd, 2-H), 2.70 (dd, 2-H), 3.80 (br d, 3-H), 3.08 (br d, 4-H), 3.51 (s, 4-OCH$_3$), 4.11 (dd, 5-H), 2.30 (m, 6-H), 0.96 (ddd, 7-H), 1.51 (ddd, 7-H), 1.92 (m, 8-H), 4.13 (dd, 9-H), 5.69 (dd, 10-H), 6.27 (dd, 11-H), 6.03 (br dd, 12-H), 5.63 (ddd, 13-H), 2.12 (ddd, 14-H), 2.53 (m, 14-H), 5.30 (ddq, 15-H), 1.32 (d, 16-H$_3$), 2.38 (dd, 17H), 2.84 (ddd, 17-H), 9.80 (br s, 18-H), 1.02 (d, 19-H$_3$), 4.49 (d, 1'-H), 3.52 (dd, 2'-H), 2.48 (br dd, 3'-H), 3.29 (m, 4'-H), 3.30 (m, 5'-H), 1.23 (br d, 6'-H$_3$), 2.51 (s, 3'-N(CH$_3$)$_2$), 5.08 (br d, 1''-H), 1.85 (dd, 2''-Hax), 2.02 (br d, 2''-Heq), 4.63 (d, 4''-H), 4.46 (dq, 5''-H), 1.15 (d, 6''-H$_3$), 1.12 (s, 7''-H$_3$), 2.31 (d, 4''-OCOCH$_2$CH(CH$_3$)$_2$), 2.15 (m, 4''-OCOCH$_2$CH(CH$_3$)$_2$), 0.98 (d, 4''-OCOCH$_2$CH(CH$_3$)$_2$).

(4) $^{13}$C NMR spectrum (100 MHz, CDCl$_3$).

δ(ppm): 174.11* (s, C-1), 37.77 (t, C-2), 68.22 (d, C-3), 85.23 (d, C-4), 61.79 (q, 4-OCH$_3$), 79.08 (d, C-5), 30.45 (d, C-6), 31.02 (t, C-7), 33.78 (d, C-8), 73.07 (d, C-9), 129.74 (d, C-10), 134.51 (d, C-11), 132.37 (d, C-12), 131.87 (d, C-13), 41.85 (t, C-14), 69.12 (d, C-15), 20.12 (q, C-16), 43.01 (t, C-17), 202.58 (d, C-18), 14.81 (q, C-19), 103.88 (d, C-1′), 71.66 (d, C-2′), 68.76 (d, C-3′), 76.03 (d, C-4′), 73.07 (d, C-5′), 18.86 (q, C-6′), 41.93 (q, 3′-N(CH$_3$)$_2$), 97.05 (d, C-1″), 41.72 (t, C-2″), 69.36 (s, C-3″), 77.00 (d, C-4″), 63.49 (d, C-5″), 17.84 (q, C-6″), 25.36 (q, C-7″), 172.96* (s, 4″-OCOCH$_2$CH(CH$_3$)$_2$), 43.34 (t, 4″-OCOCH$_2$CH- (CH$_3$)$_2$), 25.55 (d, 4″-OCOCH$_2$CH(CH$_3$)$_2$), 22.40 (q, 4″-OCOCH$_2$CH(CH$_3$)$_2$), 22.45 (q, 4″-OCOCH$_2$CH(CH$_3$)$_2$).

EXAMPLE 6

Microbial conversion of miokamycin [in formula (I), $R^1$ and $R^5$ each represents a propionyl group, $R^2$ is a hydrogen atom, $R^3$ is an acetoxy group and $R^4$ is an acetyl group] into 3″-O-acetyl-3-depropionyl-neoisomidecamycin [formula (III)] and 3″-O-acetyl-leucomycin A$_7$ [formula (IV)]:

Ten 500-ml Erlenmeyer flasks, each containing 100 ml of the production medium, were sterilized at 120° C. for 30 minutes. Miokamycin was added to each flask to a concentration of 100 μg/ml and 5 ml portions of the seed culture were inoculated therein followed by incubation at 26° C. for 7 days with shaking. After the completion of the incubation, diatomaceous earth was added as a filter aid and the incubation medium was filtered to thereby obtain 750 ml of a filtrate. The filtrate was adjusted to pH 9 and then extracted with 750 ml of ethyl acetate. The ethyl acetate layer was concentrated to dryness to obtain 62.0 mg of an oily substance. Then this oily substance was purified with preparative TLC (development system: chloroform/methanol, 10 : 1 by volume) and three active components thus obtained were separately subjected to gel filtration using 40 ml of Sephadex LH-20. Thus 5.8 mg of 3″-O-acetyl-3-depropionylneoisomidecamycin, 6.2 mg of 3″-O-acetylleucomycin A$_7$ and 15.8 mg of miokamycin were recovered.

EXAMPLE 7

100-ml Erlenmeyer flasks, each containing 20 ml of the seed medium, were sterilized at 120° C. for 30 minutes and then a platinum loopful of slant agar culture of the strain Phialophora sp. PF1086 (FERM BP-3961) was inoculated thereto. After incubating at 26° C. for 2 days with shaking, a seed culture was obtained. Ten 500-ml Erlenmeyer flasks, each containing 100 ml of the production medium, were sterilized at 120° C. for 30 minutes. Midecamycin was added to each flask to a concentration of 100 μg/ml and 5 ml portions of the seed culture were inoculated therein followed by incubation at 26′ C. for 7 days with shaking. After the completion of the incubation, diatomaceous earth was added as a filter aid and the incubation medium was filtered to thereby obtain 700 ml of a filtrate. The filtrate was adjusted to pH 9 and then extracted with 700 ml of ethyl acetate. The ethyl acetate layer was concentrated to dryness to obtain 71.5 mg of an oily substance. Then this oily substance was purified with preparative TLC (development system: chloroform/methanol, 10 : 1 by volume) and two active components thus obtained were separately subjected to gel filtration using 40 ml of Sephadex LH-20. Thus 22.1 mg leucomycin A$_7$ and 25.3 mg of midecamycin were recovered.

The present invention makes it possible to efficiently produce a 3-deacylated derivative of a 16-membered ring macrolide antibiotic using a microorganism belonging to the genus Phialophora or Preussia. As a result, a novel macrolide antibiotic or a material to be converted thereto can be easily obtained.

While the invention has been described in detail and with reference to specific examples thereof, it will be apparent to one skilled in the art that various changes and modifications can be made therein without departing from the spirit and scope thereof.

What is claimed is:

1. A method of producing a 3-deacylated derivative of a 16-membered macrolide antibiotic represented by the following general formula (II):

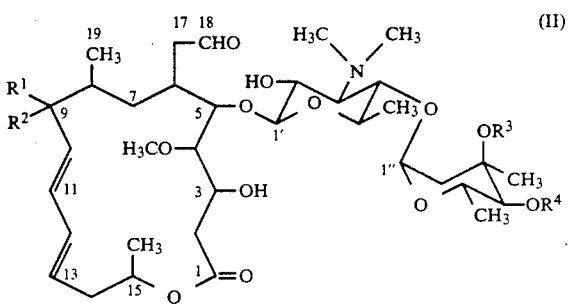

wherein $R^1$ represents a hydrogen atom; $R^2$ represents a hydroxyl group; or $R^1$ and $R^2$ form a carbonyl group together with the carbon atom to which they are bound; $R^3$ represents a hydrogen atom or an acetyl group; and $R^4$ represents a hydrogen atom, an acetyl group, a propionyl group, a butyryl group or an isovaleryl group; or formula (III):

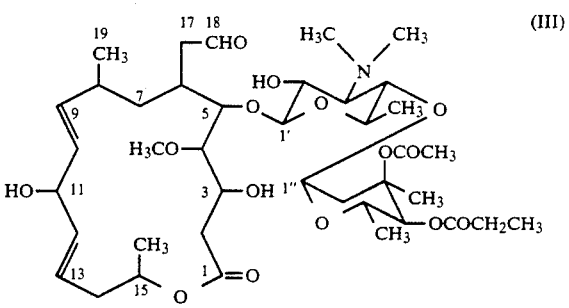

which comprises treating a 16-membered macrolide antibiotic represented by formula (I):

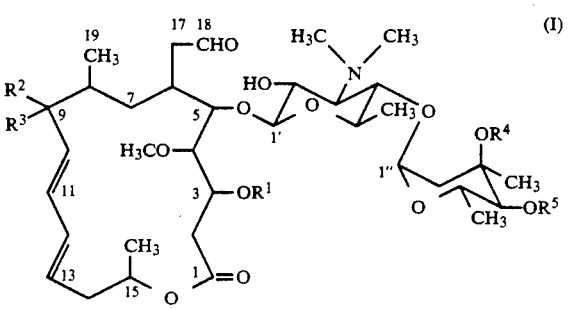

wherein $R^1$ represents an acetyl group or a propionyl group; $R^2$ represents a hydrogen atom; $R^3$ represents a hydroxyl group or an acetoxy group; or $R^2$ and $R^3$ form a carbonyl group together with the carbon atom to which they are bound; $R^4$ represents a hydrogen atom or an acetyl group; and $R^5$ represents a hydrogen atom, an acetyl group, a propionyl group, a butyryl group or an isovaleryl group; with a culture of a microorganism belonging to the genus Phialophora or Preussia or a dispersion containing washed cells of the microorganism.

2. A method according to claim 1, wherein said microorganism is Phialophora sp. PF1083 (FERM BP-3960) or Preussia sp. PF1086 (FERM BP-3961).

* * * * *